United States Patent [19]

Jung

[11] Patent Number: 4,837,303
[45] Date of Patent: Jun. 6, 1989

[54] NOVEL SOMATOSTATIN DERIVATIVES

[75] Inventor: Guenter Jung, Tuebingen, Fed. Rep. of Germany

[73] Assignee: Diamalt Aktiengesellschaft, Munich, Fed. Rep. of Germany

[21] Appl. No.: 30,810

[22] PCT Filed: Jun. 20, 1986

[86] PCT No.: PCT/DE86/00259

§ 371 Date: Feb. 25, 1987

§ 102(e) Date: Feb. 25, 1987

[87] PCT Pub. No.: WO87/00181

PCT Pub. Date: Jan. 15, 1987

[30] Foreign Application Priority Data

Jun. 25, 1985 [DE] Fed. Rep. of Germany ....... 3522638

[51] Int. Cl.$^4$ .......................... C07K 7/26; C07K 7/64; A61K 37/02
[52] U.S. Cl. ..................... 530/311; 514/10; 530/317; 530/338
[58] Field of Search ................. 514/17, 18, 19, 10; 530/311, 317, 323

[56] References Cited

U.S. PATENT DOCUMENTS

| | | | |
|---|---|---|---|
| 3,998,795 | 12/1976 | Sarantakis | 514/806 |
| 4,061,608 | 12/1977 | Sarantakis | |
| 4,118,380 | 10/1978 | Immer et al. | 530/328 |
| 4,180,500 | 12/1979 | Sarantakis et al. | 530/327 |
| 4,190,575 | 2/1980 | Sarantakis | 530/327 |
| 4,358,439 | 11/1982 | Sieber et al. | 530/311 |
| 4,439,425 | 3/1984 | Tarcsay et al. | 514/19 |

FOREIGN PATENT DOCUMENTS 0000330  6/1978  European Pat. Off. .
0114787  1/1984  European Pat. Off. .
2294715 12/1974  France .................................. 514/19

OTHER PUBLICATIONS

Chem. Abs., vol. 101, 1984, 211690s.
Somatostatin, Vale et al., pp. 365–397, (1972).
Samatostatin, Insulin & Glucagon, Brown et al., pp. 336–343.

Primary Examiner—Delbert R. Phillips
Assistant Examiner—T. D. Wessendorf
Attorney, Agent, or Firm—Millen & White

[57] ABSTRACT

Somatostatin derivatives of general Formula I

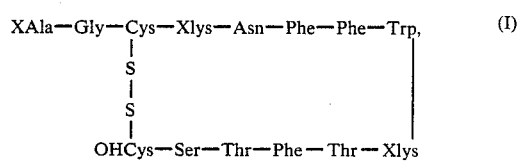

wherein at least one of the residues X represents a moiety, bound to the free amino group of alanine or lysine, of Formula II

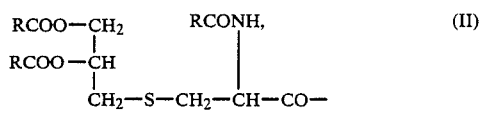

with R meaning an alkyl group containing 7–23 carbon atoms, and the residues X which may remain mean hydrogen atoms, are pharmacologically active compounds.

6 Claims, No Drawings

NOVEL SOMATOSTATIN DERIVATIVES

BACKGROUND OF THE INVENTION

The invention relates to somatostatin derivatives of general Formula I

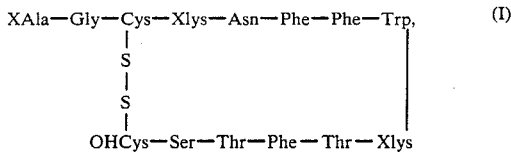

wherein at least one of the residues X represents a moiety, bound to the free amino group of alanine or lysine, of Formula II

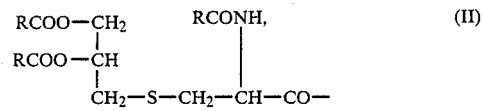

with R meaning an alkyl group containing 7–23 carbon atoms, and the residues X which may remain mean hydrogen atoms.

The invention furthermore concerns a process for the production of these somatostatin derivatives and pharmaceutical preparations containing these compounds.

As is known, somatostatin is a pharmacologically active compound utilized, inter alia, for the treatment of diabetes mellitus and gastrointestinal disorders S. M. McCann, Ann. Rev. Pharmacol. Toxicol. 1982, 22: 491–515; K. Gerbitz, Nachr. Chem. Techn. 1975, 23: 355–357; K. Gyr, Trends in Pharmacol. Sci., 1983, 3: 367–369; and S. Reichlin, N. Engl. Med. 1983, 309: 1495–1501 and 1556–1563.

Disadvantages of this compound are, inter alia, its inadequately specific activity and its rapid drop in efficacy.

SUMMARY OF THE INVENTION

The somatostatin derivatives of this invention according to general Formula I exhibit the same direction of activity as somatostatin proper, but are distinguished over this compound by a more specific effectiveness and a longer duration of activity.

The somatostatin derivatives of this invention can be produced from somatostatin and the acids of general Formula III under conditions conventionally employed in peptide synthesis for the establishment of acid amide linkages (Houben-Weyl, Methoden der organischen Chemie, Georg Thieme Publishers, Stuttgart, Fed. Republic of Germany, 4th ed, vol. XV/1, Synthesis of Peptides, part 1, 1974, pp. 28 et seq.). Thus somatostatin can be N-acylated with an acid of Formula III

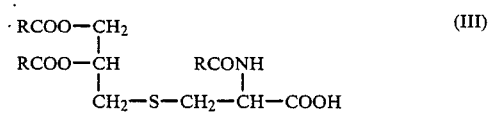

wherein R is as defined above, or with a reactive derivative thereof.

Thus, it is possible, for example, to react the carboxylic acids under the conventional conditions with somatostatin in the presence of dicyclohexylcarbodiimide, or the acids are converted into the corresponding acid chlorides or mixed anhydrides, and these are reacted with somatostatin in a manner known per se.

The acids of general Formula III utilized as the starting compounds can contain, as substituent R, alkyl groups of 7–23 carbon atoms and having equal or differing chain lengths. These alkyl groups are preferably straight-chain and exhibit an odd number of carbon atoms. Examples of alkyl groups are: the heptyl group, the nonyl group, the undecyl group, the tridecyl group, the pentadecyl group, the heptadecyl group, the nonadecyl group, the heneicosyl group and the tricosyl group.

Suitable starting compounds for the process of this invention are the following acids, for example, N-palmitoyl-S-(2[R,S],3-dilanroyloxypropyl-L-cysteine, N-palmitoyl-S-(2[R,S],3-dipalmitoyloxypropyl)-L-cysteine, N-octanoyl-S-(2[R,S],3-didecanoyloxypropyl)-L-cysteine, N-octanoyl-S-(2[R,S],3-didodecanoyloxypropyl)-L-cysteine, N-octanoyl-S-(2[R,S],3-dioctanoyloxypropyl)-L-cysteine, N-eicosanoyl-S-(2[R,S],3-dioctanoyloxypropyl)-L-cysteine, N-tetracosanoyl-S-(2[R,S],3-dioctanoyloxypropyl)-L-cysteine, and N-stearoyl-S-(2[R,S],3-distearoyloxypropyl)-L-cysteine.

The acids of general Formula III can be produced by acylation of compounds of Formula IV

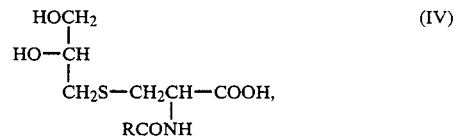

which, in turn, can be synthesized in accordance with the process described in European Patent Application No. 114787.

The compounds according to the invention can be processed into pharmaceutical preparations by adding the customary auxiliary agents and/or excipients. Thus, it is possible, for example, to convert the more hydrophilic somatostatin derivatives of general Formula I optionally with the addition of solubilizers (approximately up to 1% by weight of "Cremophor" or up to 30% by weight of propylene glycol), buffers (phosphate buffer, tris buffer), sodium chloride, etc., into aqueous injection solutions or infusion solutions. On the other hand, it is also possible to process these compounds with addition of the conventional excipients (lactose, galactose, low-molecular polyvinylpyrrolidone, etc.) into dry products which are combined with double-distilled water prior to injection or infusion. The lipophilic somatostatin derivatives of general Formula I can be converted with the use of oils (such as soybean oil) and the usual emulsifiers (such as up to 10% by weight of lecithin or a phospholipid) into oil emulsions suited for injection or infusion. Of course, the usual steps must be taken to ensure that the thus-produced preparations, containing per dosage customarily 100 μg to 5 mg of active compound, are germfree.

The preparations of this invention can be utilized, for example, for the treatment of diabetes mellitus or for the treatment of gastrointestinal disorders. The daily dosage to be usually administered is 50 μg to 200 μg of somatostatin derivative/kg of body weight.

The practical example set forth below serves for explaining the process of this invention.

EXAMPLE 200 mg of N-palmitoyl-S-(2[R,S],3-dipalmitoyloxy-propyl)-L-cysteine is combined, in 5 ml of a mixture of 2 parts by volume of dimethylformamide and 1 part by volume of chloroform, with 30 mg of butanol and 45 mg of dicyclohexylcarbodiimide and agitated for 30 minutes at 0° C. Then 90 mg of somatostatin and 16 mg of N-methylmorpholine in 5 ml of dimethylformamide-chloroform (mixture ratio as set forth above) are added to the reaction mixture, and the latter is stirred for 6 hours at room temperature.

The reaction mixture is concentrated under vacuum, the residue is purified by means of gel chromatography ("Sephadex LH 20", chloroform-methanol 1+1), and 40 mg of tri-N-[N-palmitoyl-S-(2[R,S],3-dipalmitoyl-propyl-L-cysteinyl]somatostatin is obtained.

What is claimed is:

1. A somatostatin derivative of the Formula I

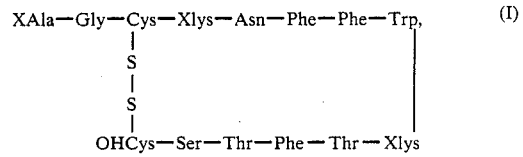

wherein at least one X is a moiety, bound to the free amino group of alanine or lysine, of Formula II

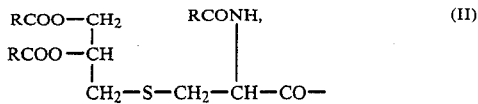

wherein R is alkyl of 7–23 carbon atoms, and all X's are hydrogen or said moiety of Formula II.

2. A somatostatin derivative of claim 1, wherein each R is n-pentadecyl or n-heptadecyl.

3. A somatostatin derivative of claim 1, wherein all X's are different from hydrogen.

4. A pharmaceutical composition comprising an amount of a somatostatin derivative of claim 1 effective to treat diabetes mellitus and a pharmaceutically acceptable carrier.

5. A somatostatin derivative of claim 2, wherein all X's are different from hydrogen.

6. A method of treating a patient suffering from diabetes mellitus comprising administering to the patient an amount of a compound of claim 1 effective for such treatment.

* * * * *